United States Patent [19]

Duffett

[11] Plant 5,167

[45] Dec. 27, 1983

[54] CHRYSANTHEMUM PLANT

[75] Inventor: William E. Duffett, Salinas, Calif.

[73] Assignee: Yoder Brothers, Inc., Barberton, Ohio

[21] Appl. No.: 356,917

[22] Filed: Mar. 10, 1982

[51] Int. Cl.[3] ..... A01H 5/00

[52] U.S. Cl. ..... Plt./79

[58] Field of Search ..... Plt./79

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant known by the cultivar name Rawhide and particularly characterized as to uniqueness by the combined characteristics of flat capitulum form; decorative capitulum type; dark bronze ray floret color; diameter across face of capitulum ranging from 90 to 115 mm. at maturity; uniform ten week photoperiodic flowering response to short days; tall plant height when grown single stem; 12.5 to 22.5 cm. peduncles on open, normally terminal sprays, and 13° C. minimum temperature tolerance for initiation and development of flowering buds.

3 Drawing Figures

The present invention comprises a new and distinct cultivar of *Chrysanthemum morifolium,* Ramat., hereinafter referred to by the cultivar name Rawhide.

Rawhide is a product of a planned breeding program which had the objective of creating new chrysanthemum cultivars with low temperature tolerance in cut spray mum programs with decorative capitulum type, dark bronze ray floret color, ten week flowering response, and having the ability to produce commercially acceptable quality in year round programs. Such traits in combination were not present in previously available commercial cultivars.

Rawhide was originated from a cross made in a controlled breeding program in Salinas, Calif. in 1978. The female parent was #58307001, Flamenco (unpatented commercial cultivar), originated by the present inventor from a hybridization of two unnamed seedlings. The male parent of Rawhide was #75235002 (unpatented), originated from a cross between two unnamed seedlings.

Rawhide was discovered and selected as one flowering plant within the progeny of the stated cross by William E. Duffett on June 15, 1979 in a controlled environment in Salinas, Calif.

The first act of asexual reproduction of Rawhide was accomplished when vegetative cuttings were taken from the initial selection in November, 1979 in a controlled environment in Salinas, Calif. by a technician working under formulations established and supervised by William E. Duffett.

Horticultural examination of selected units initiated Mar. 21, 1980 has demonstrated that the combination of characteristics as herein disclosed for Rawhide are firmly fixed and are retained through successive generations of asexual reproduction.

Rawhide has not been observed under all possible environmental conditions. The phenotype may vary significantly with variations in environment such as temperature, light intensity and day length. The observations, measurements and comparisons describe plants grown in Salinas, Calif. under greenhouse conditions which approximate those generally used in commercial practice.

The following traits have been repeatedly observed and are determined to be basic characteristics of Rawhide which in combination distinguish this chrysanthemum as a new and distinct cultivar:

(1) flat capitulum form;

(2) decorative capitulum type;

(3) bronze ray floret color;

(4) diameter across face of capitulum ranging from 90 to 115 mm. at maturity;

(5) uniform ten week photoperiodic flowering response to short days;

(6) tall plant height (65 to 90 cm.) when grown from a rooted cutting with no long days and 14 hour dark periods for March through November flowerings; and (7) tolerance of 13° C. minimum temperature for initiation and development of flowering buds.

The accompanying photographic drawings depict typical foliage and inflorescence characteristics of Rawhide. Sheet 1 is a color photograph of a plant of Rawhide grown as a cut spray, with colors being as accurate as possible with renditions of this type. Sheet 2 is a black and white photograph of three views of the inflorescence of Rawhide. Sheet 3 shows the foliage of Rawhide in three stages of growth.

Of the many commerical cultivars known to the present inventor, the most similar in comparison to Rawhide is Flame Belair disclosed in U.S. Plant Pat. No. 3,353. Reference is made to attached Chart A which compares certain characteristics of Rawhide to those same characteristics of Flame Belair.

In comparison to Flame Belair, Rawhide has a darker ray floret color, larger diameter across the face of the capitulum, flatter, non-reflexing capitulum form, and normally terminal spray formation, as contrasted with the open, frequently compound spray of Flame Belair. The response of Rawhide is more uniform than Flame Belair, being more tolerant of both high and low temperatures for initiation and development of flowering buds.

In the following description, color references are made to The Royal Horticultural Society Colour Chart. The color values were determined between 10:00 and 11:00 A.M. on Nov. 20, 1981 under 150 foot-candle light intensity at Salinas, Calif.

Classification:

*Botanical.*—*Chrysanthemum morifolium,* Ramat., cv Rawhide.

*Commercial.*—Cut spray.

I. Inflorescence:

A. *Capitulum.*—Form: Flat. Type: Decorative. Diameter across face: 90 to 115 mm.

B. *Corolla of ray florets.*—Color (General Tonality From A Distance of Three Meters): Bronze; 167-A. Color (abaxial): 170-A and B (immature) to 167-A, B and C (mature). Color (adaxial): 22-A, B and C.

C. *Reproductive organs.*—Androecium: Present disc florets only; scant pollen. Gynoecium: Present both and disc florets.

II. Plant:

A. *General appearance.*—Height: Tall, 65 to 90 cm. as a flowering plant from a rooted cutting with no long days for March through November flowerings, maintaining a minimum nightly 14 hour continuous dark period; peduncles 12.5 to 22 cm. in length.

B. *Foliage.*—Color (abaxial): 137-A and B. Color (adaxial): 138-A and B. Shape: Moderately lobed and slightly serrated.

CHART A

COMPARISON OF RAWHIDE AND FLAME BELAIR

| | RAY FLORET | CAPITULUM FORM | SPRAY |
|---|---|---|---|

CHART A-continued

COMPARISON OF RAWHIDE AND FLAME BELAIR

| CULTIVAR | COLOR | AND TYPE | FORMATION |
|---|---|---|---|
| RAWHIDE | Dark Bronze | Flat Decorative | Terminal Upright |
| FLAME BELAIR | Bronze | Flat Decorative | Terminal open, Sometimes Compound |

| CULTIVAR | DIAMETER ACROSS FACE OF CAPITULUM | PLANT HEIGHT | FLOWERING RESPONSE PERIOD |
|---|---|---|---|
| RAWHIDE | 90 to 115 mm. | Tall 65 to 90 cm. | 10 Week |
| FLAME BELAIR | 70 to 80 mm. | Tall 70 to 80 cm. | 9 Week |

COMPARISONS MADE OF PLANTS GROWN AS SINGLE STEM CUT SPRAYS IN SALINAS, CALIFORNIA

I claim:

1. A new and distinct plant of *Chrysanthemum morifolium,* Ramat., known by the cultivar name of Rawhide, as described and illustrated, and particularly characterized as to uniqueness by the combined characteristics of flat capitulum form; decorative capitulum type; dark bronze ray floret color; diameter across face of capitulum ranging from 90 to 115 mm. at maturity; uniform ten week flowering response; tall plant height when grown single stem; 12.5 to 22.5 cm. peduncles; normally terminal sprays, and 13° C. minimum temperature tolerance for initiation and development of flowering buds.

* * * * *

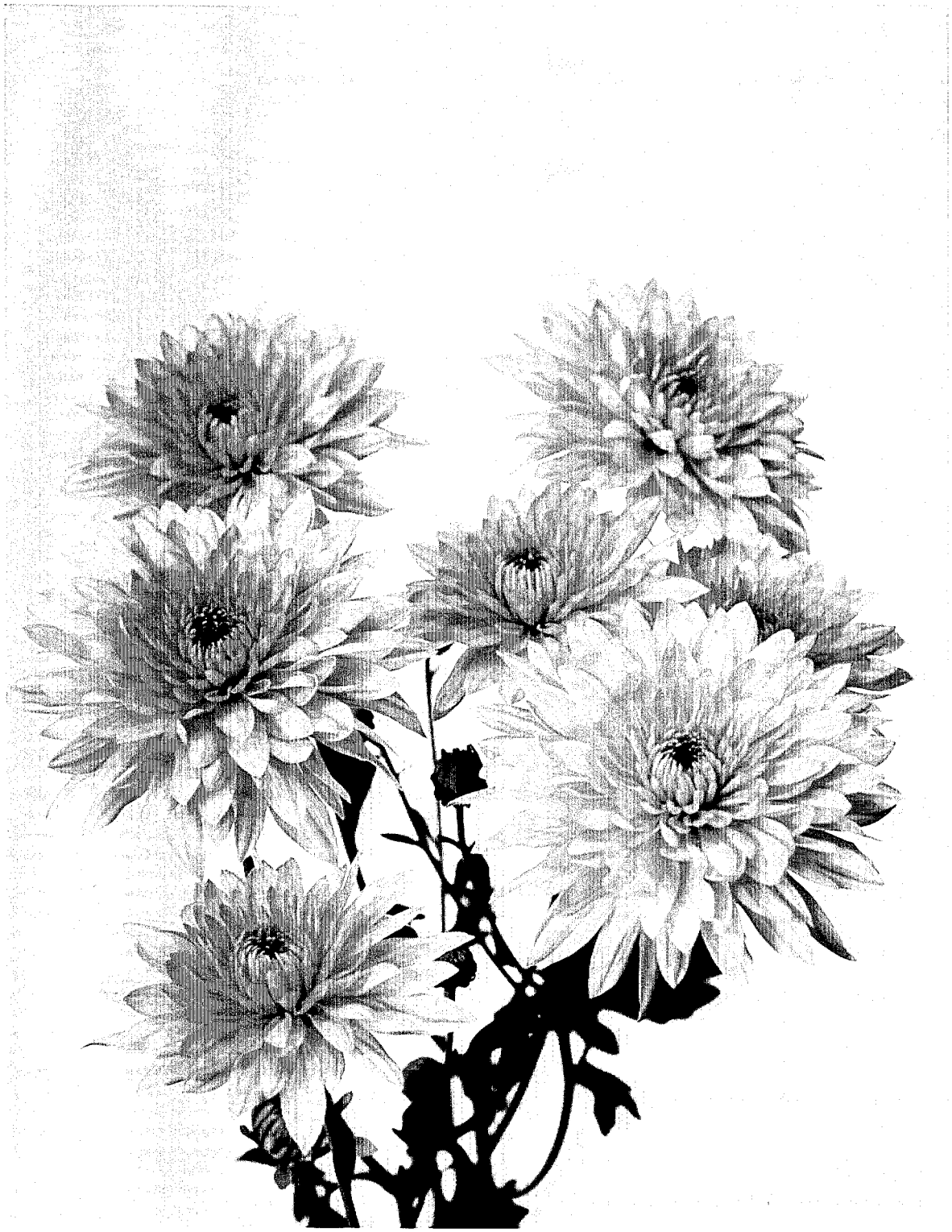

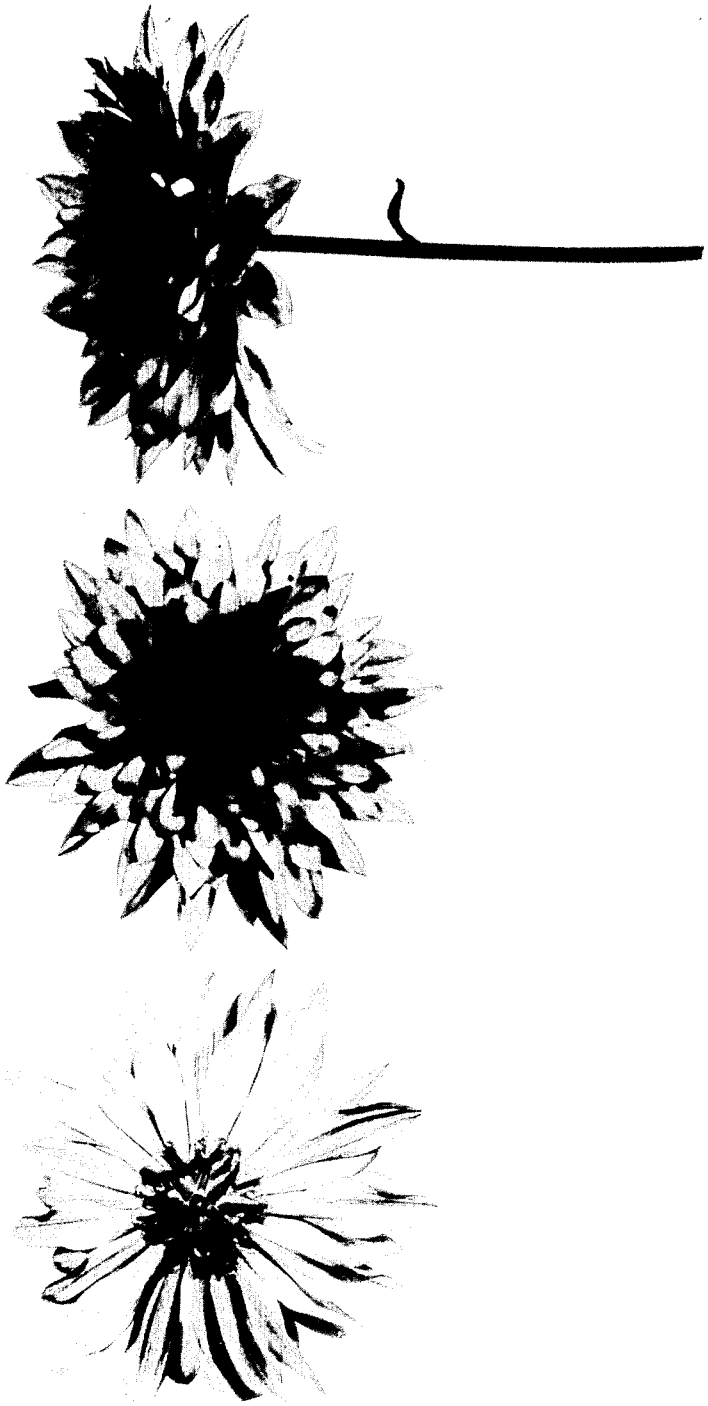

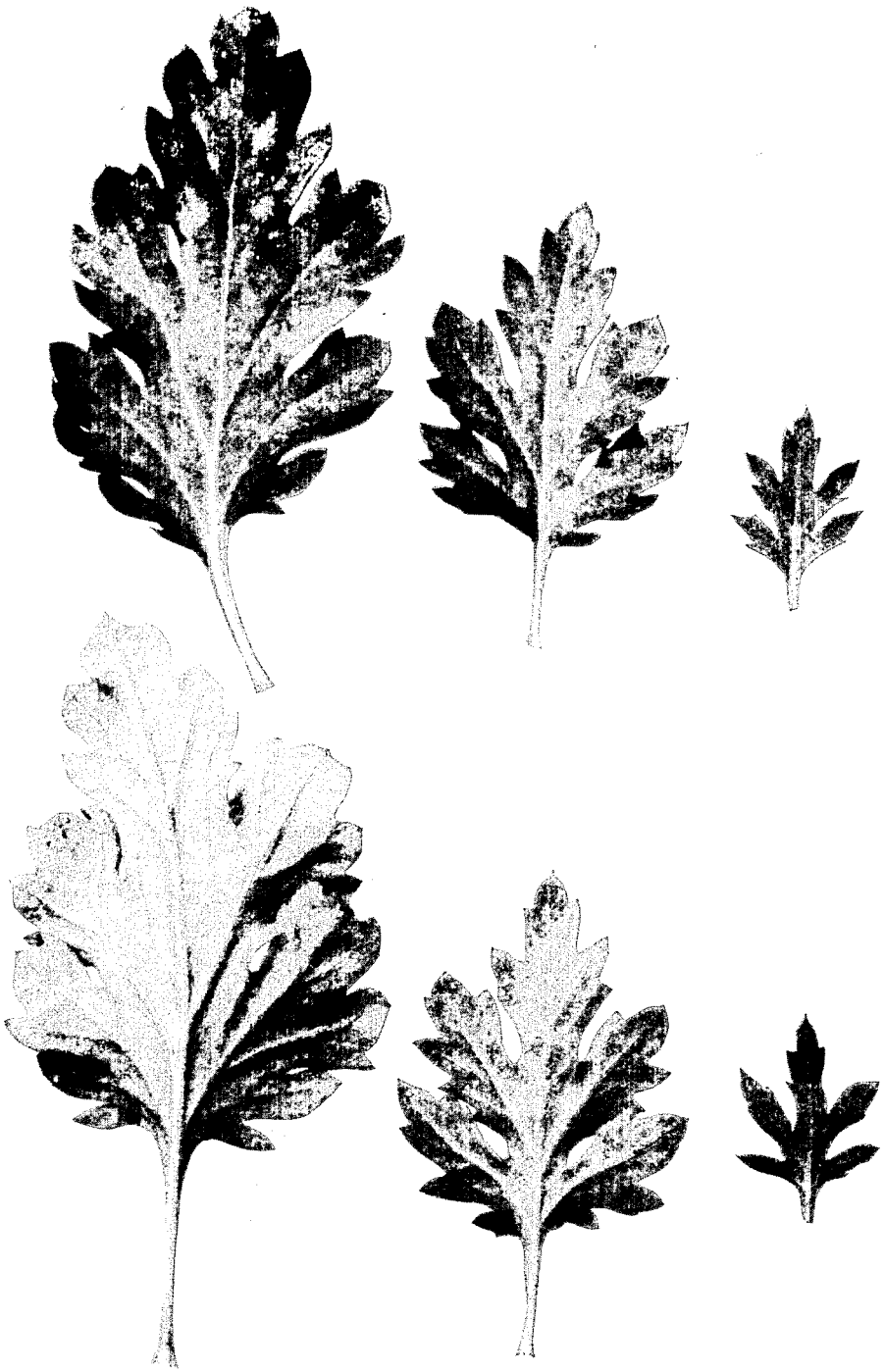

UNITED STATES PATENT AND TRADEMARK OFFICE

CERTIFICATE OF CORRECTION

PATENT NO. : PP 5167

DATED : December 27, 1983

INVENTOR(S) : William E. Duffett

It is certified that error appears in the above—identified patent and that said Letters Patent is hereby corrected as shown below:

--In column 3, line 16, after "both", insert --ray--.

--In column 3, line 25, change "22 cm." to --22.5 cm.--.

Signed and Sealed this

Tenth Day of April 1984

[SEAL]

Attest:

GERALD J. MOSSINGHOFF

Attesting Officer

Commissioner of Patents and Trademarks